United States Patent
Dirckx

(10) Patent No.: US 8,638,997 B2
(45) Date of Patent: Jan. 28, 2014

(54) METHODS AND SYSTEMS FOR MEDICAL IMAGE PROCESSING, RETRIEVAL, AND REVIEWING

(75) Inventor: Conrad Dirckx, Marston (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 22 days.

(21) Appl. No.: 13/301,956

(22) Filed: Nov. 22, 2011

(65) Prior Publication Data

US 2012/0134554 A1    May 31, 2012

(30) Foreign Application Priority Data

Nov. 26, 2010 (GB) .................................. 1020079.8

(51) Int. Cl.
*G06K 9/00* (2006.01)
(52) U.S. Cl.
USPC .......................................................... 382/128
(58) Field of Classification Search
None
See application file for complete search history.

(56) References Cited

U.S. PATENT DOCUMENTS

| 5,807,256 A | 9/1998 | Taguchi et al. |
| 7,873,526 B2* | 1/2011 | Iwasa et al. ........................ 705/2 |
| 2006/0230049 A1 | 10/2006 | Yeluri et al. |
| 2008/0212856 A1* | 9/2008 | Oosawa et al. ............... 382/128 |
| 2009/0022377 A1 | 1/2009 | Matsue et al. |
| 2011/0029326 A1* | 2/2011 | Venon ............................... 705/3 |

FOREIGN PATENT DOCUMENTS

| EP | 1887487 A2 | 2/2008 |
| WO | 2005017806 A1 | 2/2005 |
| WO | 2005027015 A2 | 3/2005 |

* cited by examiner

*Primary Examiner* — Stephen R Koziol
*Assistant Examiner* — Amandeep Saini
(74) *Attorney, Agent, or Firm* — Schiff Hardin LLP

(57) ABSTRACT

In a medical image processing and retrieval system or method, an image processing system is configured to obtain a set of medical image data and to process the medical image data using at least one interpretation tool. A database is configured to store interpretation information generated in processing the medical image data using the interpretation tool. A viewing server is configured in response to a user interface instruction to retrieve from the database the interpretation information generated in processing the medical image data and to identify the at least one interpretation tool to the user interface.

11 Claims, 2 Drawing Sheets

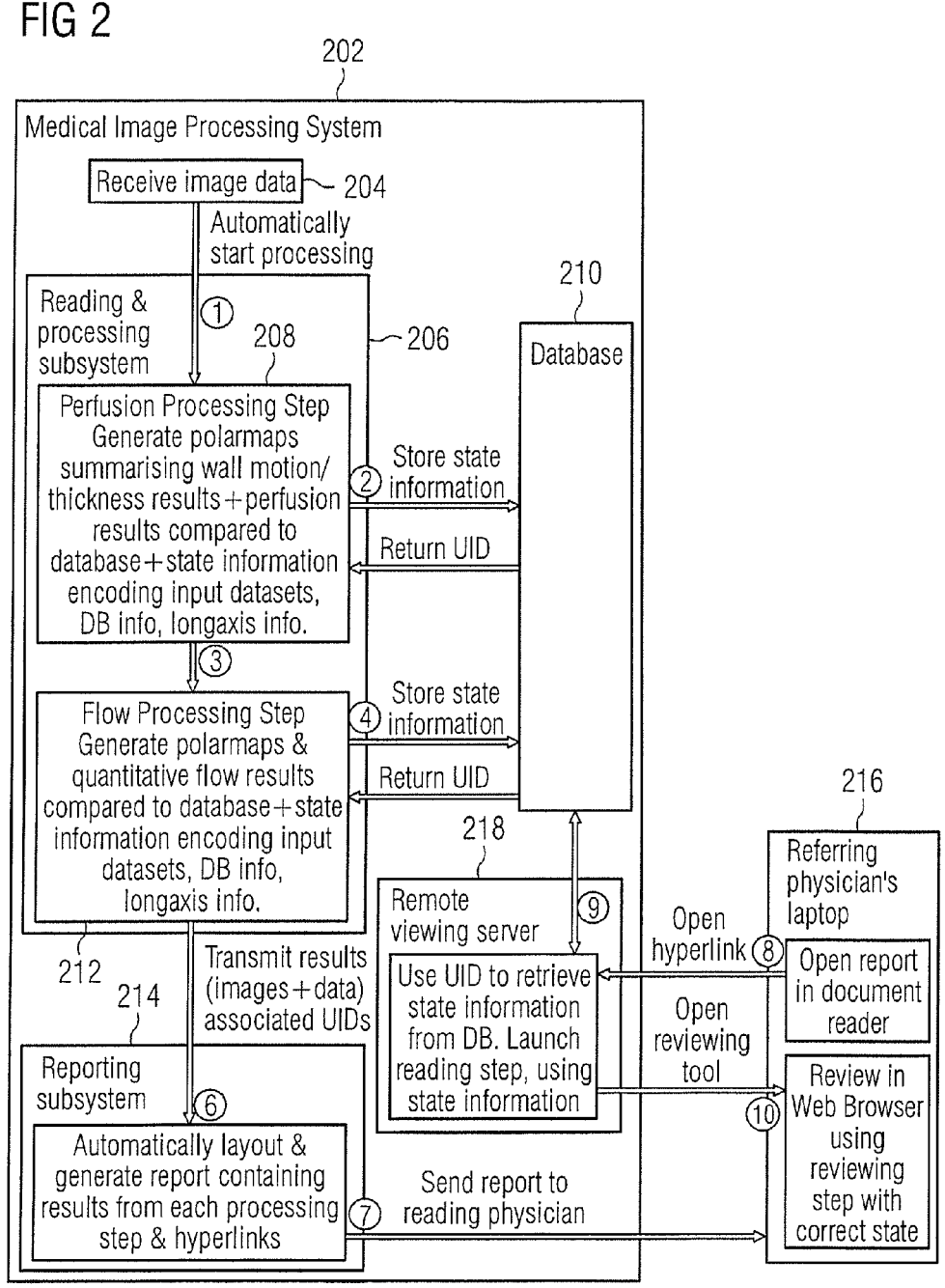

METHODS AND SYSTEMS FOR MEDICAL IMAGE PROCESSING, RETRIEVAL, AND REVIEWING

BACKGROUND

This disclosure is directed to methods and systems for medical image processing, retrieval and reviewing.

In the medical imaging field, several imaging schemes are known. Results or findings from scans from such imaging schemes are usually captured in medical imaging study reports.

When reviewing a medical imaging study report, it can sometimes be desirable to review the original data (for example, the PET image data) used to generate a particular finding/conclusion. However, this is a time-consuming process with no guarantee of being able to reproduce the same reading/processing context as when the original study was made.

Typically, the imaging data used to generate the report can be retrieved by the referring physician from an archival system, such as a PACS. The report typically includes key images related to a finding and so the referring physician can manually scroll through image slices (in the example of a 3D image volume) in the archive in an attempt to match the same image as found in the report. If they have access to the appropriate image interpretation or workflow tools, such as a ruler (in the case of a lesion size) or a cardiac database comparison tool (in the case of a nuclear cardiac study) they can attempt to reproduce the measurement on the basis information contained in the report. However, there is no guarantee that the same database would be used, the same image orientation would be used, and that other factors will be the same or even close to that used for the original finding. Therefore, the physician can have difficulty producing the same measurement or finding from the archive data as is on the report.

SUMMARY

It is an object to address these problems and provide improvements.

In a medical image processing and retrieval system or method, an image processing system is configured to obtain a set of medical image data and to process the medical image data using at least one interpretation tool. A database is configured to store interpretation information generated in processing the medical image data using the interpretation tool. A viewing server is configured in response to a user interface instruction to retrieve from the database the interpretation information generated in processing the medical image data and to identify the at least one interpretation tool to the user interface.

BRIEF DESCRIPTION OF THE DRAWINGS

FIGS. 1 and 2 are schematic diagrams illustrating systems according to exemplary embodiments.

DESCRIPTION OF THE PREFERRED EMBODIMENTS

Figure 1:
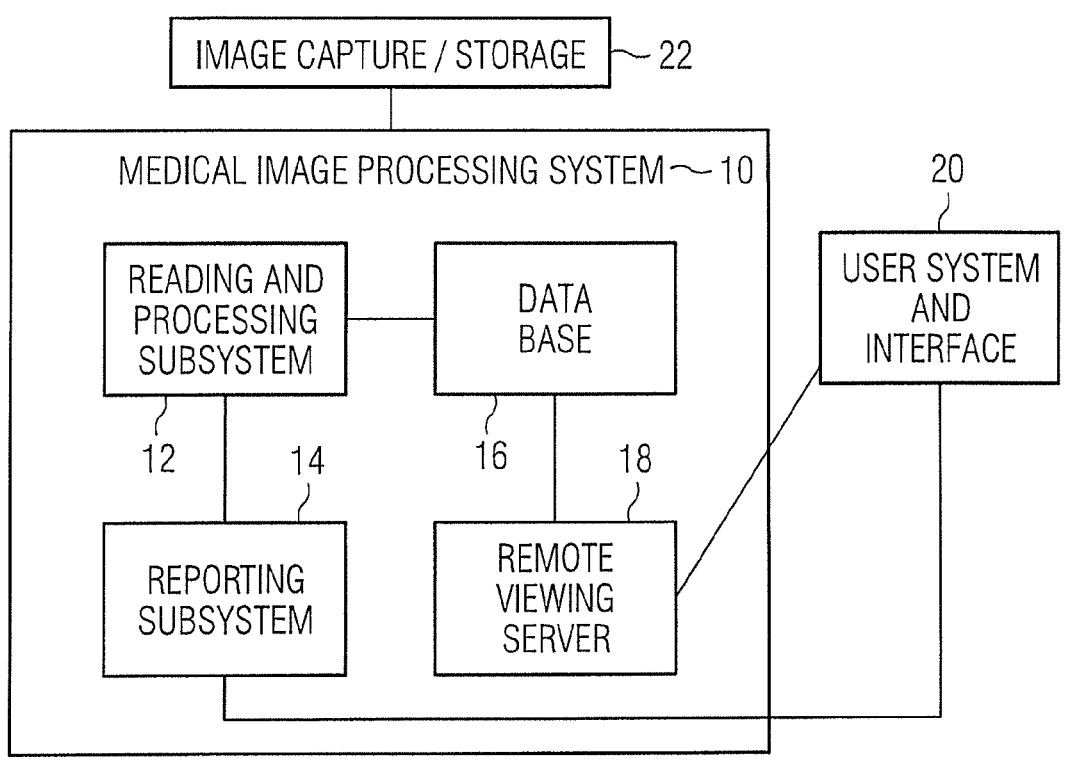

For the purposes of promoting an understanding of the principles of the invention, reference will now be made to preferred exemplary embodiments/best mode illustrated in the drawings and specific language will be used to describe the same. It will nevertheless be understood that no limitation of the scope of the invention is thereby intended, and such alterations and further modifications in the illustrated embodiments and such further applications of the principles of the invention as illustrated as would normally occur to one skilled in the art to which the invention relates are included.

In general terms, one exemplary embodiment can provide a medical image processing and retrieval system, comprising: an image processing system configured to: obtain a set of medical image data and process the medical image data using at least one interpretation tool; a database configured to store interpretation information generated in processing the medical image data using the at least one interpretation tool; and a viewing server configured to, in response to a user interface instruction, retrieve from the database the interpretation information generated in processing the medical image data, and identify the at least one interpretation tool to the user interface.

This system allows a user to reproduce a reading context for a medical image finding, rather than simply the image itself.

Preferably, the system comprises an identification system configured to generate a unique identifier for the interpretation information. More preferably, the database is further configured to store the unique identifier with the interpretation information.

Suitably, the system further comprises a reporting system configured to receive the processed image data and the interpretation information and generate a medical report containing the processed image data, and a hyperlink initiating the instruction to the viewing server.

In an exemplary embodiment, the hyperlink is associated with the unique identifier for the interpretation information.

In another exemplary embodiment, the viewing server is configured to serve to the user the interpretation information and/or the at least one interpretation tool.

Suitably, the image processing system comprises a user processing interface, and is further configured to process the medical image data using the interpretation tool under instruction from a user via the user processing interface.

In one second exemplary embodiment a method is provided to process medical image data, comprising the steps of: obtaining a set of medical image data; processing the medical image data using at least one interpretation tool; and storing in a database interpretation information generated in processing the medical image data using the interpretation tool.

Preferably, the method further comprises, in response to a user interface instruction: retrieving from the database the interpretation information generated in processing the medical image data; and identifying the at least one interpretation tool to the user interface.

In one third exemplary embodiment a method is provided for reviewing medical image data, comprising the steps of: by a user interface instructing a remote viewing server to retrieve from a database stored interpretation information generated in processing medical image data using at least one interpretation tool; receiving an identification of the at least one interpretation tool; and loading the at least one interpretation tool with the processed image data and the interpretation information onto a reviewing interface.

Preferably, the step of instructing further comprises clicking a hyperlink in a medical report which initiates the instruction to the remote viewing server.

In an exemplary fourth embodiment a medical image reviewing system is provided, comprising: a user interface configured to, in response to a user command, instruct a remote viewing server to retrieve from a database stored interpretation information generated in processing medical image data using at least one interpretation tool and to receive an identification of the at least one interpretation tool; and a reviewing interface configured to load the at least one interpretation tool with the processed image data and the interpretation information.

Suitably, in a system or method according to exemplary embodiments, the interpretation information comprises parameters of the interpretation tool used in the processing of the medical image data.

Further aspects of the exemplary embodiments comprise computer programs which, when loaded into or run on a computer, cause the computer to become a system, or to carry out methods, according to the aspects described above.

The above aspects and exemplary embodiments may be combined to provide further aspects and exemplary embodiments.

The exemplary embodiments will now be described by way of example with reference to the accompanying drawings. And when the following terms are used herein, the accompanying definitions can be applied:

PET—Positron Emission Tomography
ROI—Region of Interest
SUV—Standardised Uptake Value
PACS—Picture Archiving and Communication System
DICOM—Digital Imaging and Communications in Medicine
DICOM SeriesUID—unique identifier used to refer to a set of medical images The exemplary embodiments involve systems which combine a medical image review and processing sub-system, a report generation sub-system, a database and a remotely accessible web server providing (thin client) access to reviewing tools.

Exemplary embodiments can provide systems that give the ability to quickly and accurately reproduce the reading context of a medical image finding/result from a standard clinical assessment report. These systems use in the embodiments a number of processing steps that store their complete state when a finding is created; a database that associates this state with unique identifiers; a report generation subsystem which generates reports in standard document formats containing embedded hyperlinks and a remote viewing server that is capable of receiving HTML requests initiated by clicking on these links which contain uniqueIDs and serving the appropriate data and reading tools to the remote client computer.

Previously considered systems have only been able to provide the image in the report, perhaps a link to the original image, and perhaps some patient information linked to the image, or to the report. This sort of system is therefore devoid of the complete reading environment which was available to the original reading technician/physician.

In contrast, the exemplary embodiment can provide not only the image, but in addition some of the interpretation made in the original finding. This gives the later physician a higher order of information, not only what is in the image and the finding, but exactly what analysis and interpretation of the image was made in order to arrive at that finding. For example, rather than simply being presented with an image containing suspected lesions (alongside a finding explaining the lesions), the user of exemplary embodiments herein can have the relevant interpretation tool automatically launched (for example, on clicking the hyperlink in the report), and the tool automatically loaded with the relevant information. This could be a lesion-specific tool that the original physician was using to interpret the image, and the interpretation information loaded automatically could be the precise window-level, or threshold, or segmentation arrangement used by the original physician to come to the finding in the report.

The later remote viewing reader of the report therefore can make potentially more accurate use of the report, which can remove potential sources of error in using or interpreting the report.

A basic implementation of the systems is shown in FIG. 1. A medical image processing system 10 comprises a reading and processing sub-system 12, a database 16, a reporting sub-system 14, and a remote viewing server 18. Image data may be stored in the database 16, or may be input from image data storage or an image data capture device 22. The reading and processing subsystem provides data to the database, and to the reporting subsystem. The remote viewing server obtains data from the database. A user system and interface 20 receives information from the reporting subsystem 14, and can access the remote viewing server 18.

The reading and processing subsystem 12 uses interpretation tools (such as window level, view type, segmentation, thresholding), and the interpretation information from the use of the tools (e.g. the set window level, the view type finalised, any segmentation, a threshold value) for that processing of the image data is stored in the database. Thus, when the user interface is used to access the viewing server 18, the user can view not only the image selected in a report (from the reporting subsystem 14), but also the interpretation information that was generated during processing of that image. This can be used in the relevant interpretation tool, so that the user is effectively placed back in the reviewing environment of the original finding. If needed, the image in question can also be retrieved from the database, instead of or in addition to the copy in the report.

One specific exemplary embodiment shown in FIG. 2 uses the example of a cardiac clinical assessment report, reviewed by a referring physician. When the image data 204 is received by the medical image processing system 202 and passed to the reading and processing subsystem 206 it passes through a perfusion processing step 208 and a flow processing step 212. During each of these steps, the reading physician will use the tools presented by that step to make adjustments prior to the generation of summary images and quantitative results for inclusion in the report. As each result is generated, the complete state of that processing step (i.e. all the parameters or positions of each of the review/interpretation tools used in each part of the step) is saved into the database 210. The database returns a UID that can be used to retrieve that state information.

When all processing steps are completed, the clinical findings (results) are combined into a report by the report generation subsystem 214. For every result that is written into the report, a corresponding hyperlink is embedded with that content that contains the associated data UID.

When complete, the report is sent to the referring physician's system (here laptop 216) for review. For any of the results/findings that he wishes to query in more depth, he is able to click on the associated hyperlink and this will initiate a communication with the remote viewing server 218. The remote server presents the image data used to generate the report together with all the appropriate tools in the same reading context as was used to generate the result via a web-deployed thin-client interface.

For each of the steps used to generate a report finding, the exact state of that processing step at the moment of result generation is saved into the database along with a unique indentifier UID which is the key to retrieve this state information. This UID is also associated with the report finding as it is passed to the report generation sub-system.

Certain of the processing steps may be automatic, and others manual. For example, a window level may be optimized according to some standard or calibrated reference, or a segmentation may be automatic, whereas a threshold may be varied manually and a final value chosen manually.

The reporting subsystem will combine each finding into a report in a standard electronic document format (such as PDF) and each finding area of the report will be associated with a hyperlink in HTML format to the image review webserver and the UID associated with that findings context.

This report can then be distributed electronically & read by any standard document reading software (such as a PDF reader). However, clicking on any finding will invoke the hyperlink to the image reading software which is able then to launch the correct image processing/review tool and reproduce the exact context of that read by retrieving the state information associated with a particular finding.

For example, if a report contained a cardiac perfusion polarplot finding then at the time this polarplot was generated, the following state information would be generated.
 Cardiac Processing Engine used
 DICOM SeriesUID of the input datasets
 Long axis position
 Database used for comparison
 Color lookup table selected
 Window level selected.

This information would be stored in the database along with the UID associated with this state (for example UID_Card_ABCDE_12345)

The polarplot in the report would be associated with a link.

In one embodiment, the system can be used also to generate a draft report which is reviewed by the reading physician, and where the hyperlink invokes the processing tools that can be used to modify a result, prior to signing.

The whole system can be made able to manage the data lifecycle such that if the stored state information refers to imaging data that is no longer in the database then this could either be automatically retrieved from a PACS or the user informed that the data is no longer accessible.

In one exemplary embodiment, the reading and processing subsystem and/or the database and/or the remote viewing server may actually be housed in different systems. For example, the findings may have been made on a processing system in one location, and the reports generated and sent out and the interpretation information stored. The stored information may then be transferred to another site if necessary, for association with a viewing server at that site. The user can still access the information needed at the server, as at this stage the server merely requires the stored information on the server (not the report generator or the interpretation and processing subsystem.

In alternatives, the report can be created using any other type of standard document format (eg. MS Word). The reading tools can be provided to the client machine via a thin web-interface or via a rich-thin client installation.

The above exemplary embodiments of the invention may be conveniently realized as a computer system suitably programmed with instructions for carrying out the steps of the methods according to the respective embodiment.

For example, a central processing unit may receive the image data. For example, in one exemplary embodiment, the processor performs such steps as obtaining a set of medical image data; processing the medical image data using at least one interpretation tool; and storing in a database interpretation information generated in processing the medical image data using the interpretation tool.

Software applications loaded on a memory may be are executed to process the image data in, for example, a random access memory.

It will be appreciated by those skilled in the art that the invention has been described by way of example only, and that a variety of alternative approaches may be adopted without departing from the scope of the invention, as defined by the appended claims. And although preferred exemplary embodiments are shown and described in detail in the drawings and in the preceding specification, they should be viewed as purely exemplary and not as limiting the invention, It is noted that only preferred exemplary embodiments are shown and described, and all variations and modifications that presently or in the future lie within the protective scope of the invention should be protected.

I claim as my invention:

1. A medical image processing and retrieval system, comprising:
   an image processing system configured to obtain medical image data and to process the medical image data by a first user using interpretation tools on said medical image data to generate a report concerning said medical image data;
   a database configured to store interpretation information for all interpretation tools used to generate the report and parameters or positions of each of the interpretation tools used for the generation of said report by said first user, said interpretation tools comprising at least one of window level, view type, segmentation, and thresholding; and
   a viewing server having a user interface and configured in response to a user interface instruction by a second user to retrieve said report and also to allow retrieval from the database of said medical image data, all of said interpretation tools, all of said parameters or positions of each of the interpretation tools, and all of said stored interpretation information used for the generation of said report when the second user activates at least one link in said report to allow the second user to process the images with the same interpretation tools as the first user who generated said report.

2. The system according to claim 1 further comprising an identification system configured to generate a unique identifier for the interpretation information.

3. The system according to claim 2 wherein the database is further configured to store the unique identifier with the interpretation information.

4. The system according to claim 2 further comprising a reporting system configured to receive the processed image data and the interpretation information; and
   said second user at said user interface initiating an instruction by at least one hyperlink to the viewing server to retrieve said interpretation information.

5. The system according to claim 4 wherein the hyperlink is associated with the unique identifier for the interpretation information.

6. The system of claim 1 wherein all of the interpretation tools can be provided to said second user at said user interface.

7. The system of claim 1 wherein the second user obtaining said report at said user interface and by clicking on one or more hyperlinks in said report said second user can obtain said interpretation information.

8. The system of claim 1 wherein the second user at said user interface can receive an identification of all of the interpretation tools and said user interface being configured to load the interpretation tools with the processed image data and the interpretation information.

9. A method for processing medical image data, comprising the steps of:
provRecognitioning an image processing system configured to obtain medical image data and for processing the medical image data by a first user using interpretation tools on said medical image data to generate a report concerning said medical image data;
providing a data base configured to store interpretation information for all interpretation tools used to generate the report and parameters or positions of each of the interpretation tools used for generation of said report by said first user, said interpretation tools comprising at least one of window level, view type, segmentation, and thresholding;
providing a viewing server having a user interface and configured in response to a user interface instruction by a second user to retrieve said report; and
said second user downloading said report at said user interface, and at said user interface said user being allowed to retrieve from the data base by use of said viewing server after downloading said report said medical image data, all of said interpretation tools, all of said parameters or positions of each of the interpretation tools, and all of said stored interpretation information used for generation of said report to allow the second user to process the images with the same interpretation tools as the first user who generated said report.

10. A non-transitory computer readable medium having a computer program tangibly embodied thereon, said computer program, when executed by a computer, processing medical image data by performing the steps of:
providing an image processing system configured to obtain medical image data and for processing the medical image data by a first user using interpretation tools on said medical image data to generate a report concerning said medical image data;
providing a data base configured to store interpretation information for all interpretation tools used to generate the report and parameters or positions of each of the interpretation tools used for generation of said report by said first user, said interpretation tools comprising at least one of window level, view type, segmentation, and thresholding;
providing a viewing server having a user interface and configured in response to a user interface instruction by a second user to retrieve said report; and
said second user downloading said report at said user interface, and at said user interface said user being allowed to retrieve from the data base by use of said viewing server after downloading said report said medical image data, all of said interpretation tools, all of said parameters or positions of each of the interpretation tools, and all of said stored interpretation information used for generation of said report to allow the second user to process the images with the same interpretation tools as the first user who generated said report.

11. A medical image processing and retrieval system, comprising:
an image processing system configured to obtain medical image data and to process the medical image data by a first user using interpretation tools on said medical image data to generate a report concerning said medical image data;
a database configured to store interpretation information for all interpretation tools used to generate the report and of each of the interpretation tools used for the generation of said report by said first user, said interpretation tools comprising at least one of window level, view type, segmentation, and thresholding; and
a viewing server having a user interface and configured in response to a user interface instruction by a second user to retrieve said report and also to allow retrieval from the database of said medical image data, all of said interpretation tools, all of said parameters or positions of each of the interpretation tools, and all of said stored interpretation information used for the generation of said report when the second user activates at least one link in said report to allow the second user to process the images with the same interpretation tools as the first user who generated said report.

* * * * *